United States Patent [19]

Imonti et al.

[11] Patent Number: 4,925,450
[45] Date of Patent: May 15, 1990

[54] SURGICAL ASPIRATOR CANNULA

[75] Inventors: Maurice M. Imonti, Dana Point; Charles E. Beuchat, Irvine, both of Calif.

[73] Assignee: The Cooper Companies, Inc., Menlo Park, Calif.

[21] Appl. No.: 171,431

[22] Filed: Mar. 21, 1988

Related U.S. Application Data

[63] Continuation-in-part of Ser. No. 28,504, Mar. 20, 1987, Pat. No. 4,784,649, which is a continuation-in-part at PCT US 87/9818 filed Jul. 30, 1987.

[51] Int. Cl.$^5$ ............................................. A61M 5/325
[52] U.S. Cl. ..................................... 604/240; 604/248; 604/902
[58] Field of Search ............... 604/240, 247, 248, 119, 604/118, 242, 243, 902, 241

[56] References Cited

U.S. PATENT DOCUMENTS

| | | | |
|---|---|---|---|
| 1,520,508 | 12/1924 | Platt et al. | 604/241 |
| 3,071,402 | 9/1959 | Lasto et al. | 604/902 |
| 3,461,870 | 8/1969 | Linge | 604/118 |
| 3,517,669 | 6/1970 | Buono et al. | 604/119 |
| 3,527,478 | 9/1970 | Enssle | 285/38 |
| 4,182,385 | 1/1980 | Williamson | 604/902 |
| 4,369,991 | 1/1983 | Linder | 285/38 |
| 4,536,180 | 8/1985 | Johnson | 604/268 |
| 4,568,332 | 2/1986 | Shippert | 604/119 |

FOREIGN PATENT DOCUMENTS

| | | | |
|---|---|---|---|
| 106474 | 1/1939 | Australia | 604/241 |
| 2323925 | 11/1974 | Fed. Rep. of Germany | 128/229 |
| 3347834 | 4/1985 | Fed. Rep. of Germany | 604/119 |

Primary Examiner—John D. Yasko
Attorney, Agent, or Firm—Vorys, Sater, Seymour and Pease

[57] ABSTRACT

A surgical aspirator cannula including an elongated body member having a longitudinal aspiration conduit, and a valve assembly supported by the body member and operable to close off the aspiration conduit. The valve assembly includes a thumb switch pad and a plunger having a bore laterally therethrough. When the switch pad is depressed the bore is aligned with the aspiration conduit and suction pressure communicates with the cannula. By sliding it forward, the switch pad can be locked into this open position. When released the plunger is biased upward by a coil spring so that the bore is no longer aligned with the conduit and thereby closing it. A securing assembly removably secures the desired cannula to the forward end of the elongated body member. A generally tubular hub of the securing assembly is pressed fitted into the forward bore of the elongated body member. A ring lock encircles the hub and is rotatable with respect thereto. Forward slots in the hub assembly and the ring lock can be aligned and when aligned the radial pin of the cam lock of a cannula is inserted therein. When the ring lock is then turned the cannula via its locking pin is brought rearward towards and secured to the body member.

60 Claims, 10 Drawing Sheets

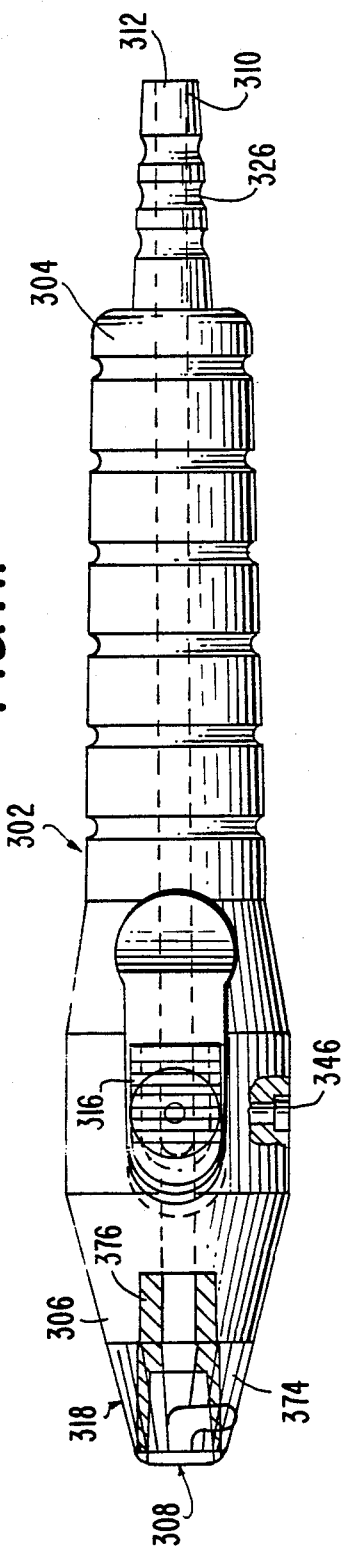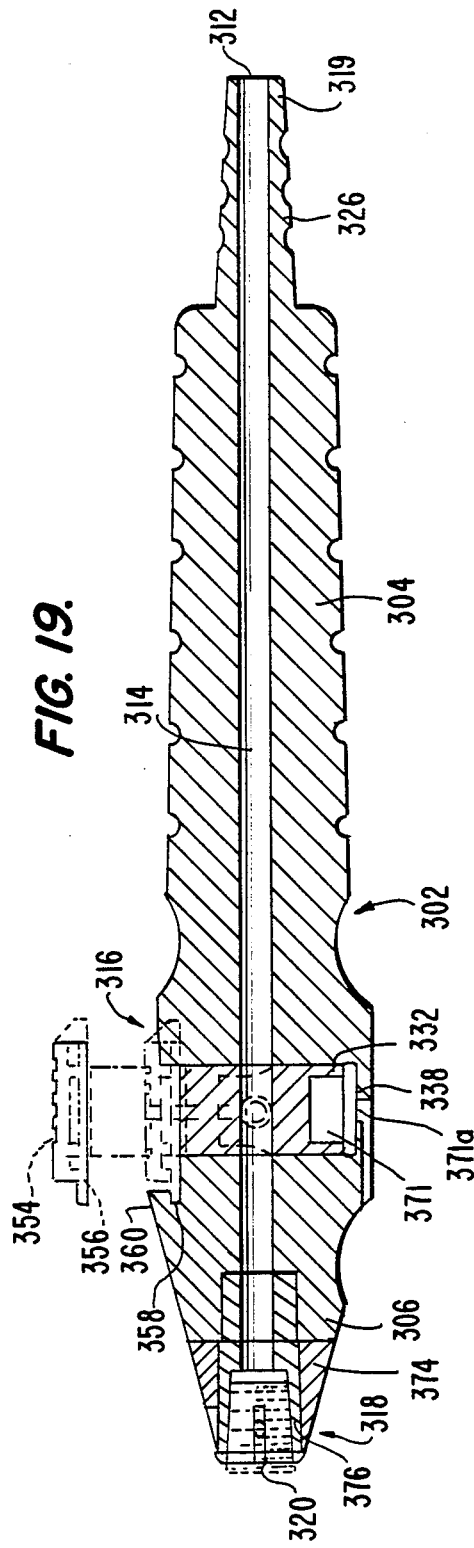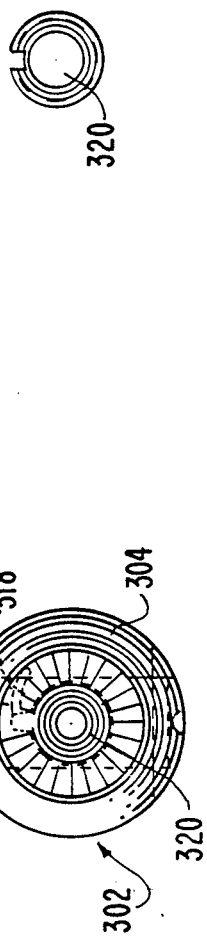

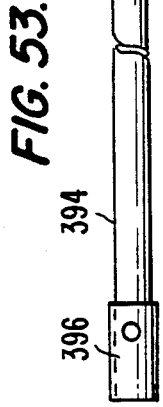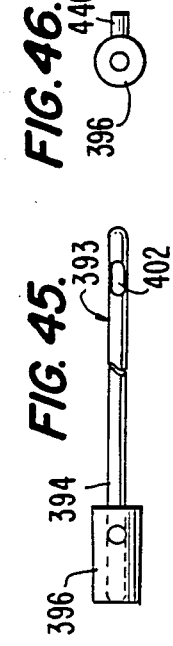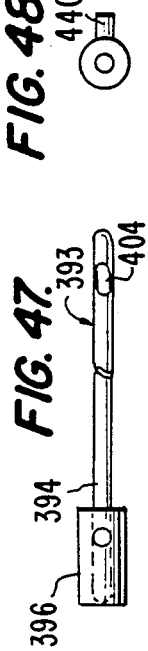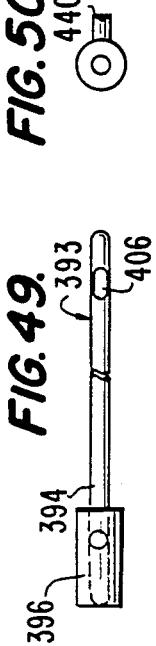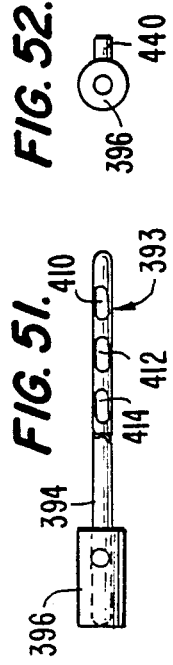

SURGICAL ASPIRATOR CANNULA

BACKGROUND OF THE INVENTION

This application is a continuation-in-part of copending application Ser. No. 028,504, filed Mar. 20, 1987, now U.S. Pat. No. 4,784,649 and International application No. PCT/US87/01818, filed July 30, 1987, the entire contents of both of which are hereby incorporated by reference.

The present invention relates to aspiration systems and methods used in medical surgery, and cannula designs therefor.

Surgical aspirator cannulas or vacuum curets have been used for many years to remove fluids and/or tissue from the body. A history of this procedure is set forth in U.S. Pat. No. 4,536,180, whose entire contents are hereby incorporated by reference. They typically comprise a hollow tube or cannula having openings at each end with the rear opening attached to a source of vacuum. The opposite end is then introduced into that portion of the body from which the fluid and/or tissue is to removed. Then when the vacuum is applied, the fluids and/or tissue are aspirated or sucked up through the opening in the opposite end and the hollow portion of the curet into a collecting container. These vacuum curets have been used in numerous medical procedures but more recently have been used in lipexheresis. This technique has become widely accepted in the medical community and practiced by physicians of many different specialities to remove fat from all over the body. Since the body contains a limited number of fat cells which do not regenerate, when the fatty tissue is removed by this suction procedure the body part becomes thinner.

One widely practiced procedure is to remove an entire layer of regular deep fat to create a layer of space in the body which space layer is then compressed to form a thinner body part. In other words, the suction lipolysis procedure permanently removes from the body localized "fatty deposits", which are difficult or impossible to remove by conventional methods of weight reduction. A probe or cannula inserted into the body breaks up the fat globules, a suction is then applied to suck the loosened fat globules out of the body. These probing and sucking procedures are repeated until the desired amount of fat has been removed.

Many surgical aspirator cannulas constructions are known, and they typically require that the cannula have a threaded distal end which fits into a threaded nut at the distal end of the handle. This design does not provide an interchangeable cannula system but rather is constructed as the means by which the manufacturer assembles the cannula. In fact to remove this cannula from the handle requires special tooling. Thus no cannula construction is known which provides for the satisfactory interchanging of different cannula configurations by the surgeon during the medical procedure. However, it is frequently desired that differently configured cannulas be used during a single medical procedure in particular for suction of fatty tissue from the upper torso. For this procedure different lengths and diameters of cannulas as well as differently configured tip shapes and openings, such as round and square, are used at different stages of the procedure. In fact it is not uncommon for a surgeon to use three different types or styles of cannulas during a single surgical procedure. No aspirator cannula design is known which provides for the easy and quick interchangeability of cannulas by the surgeon during the medical procedure in a sterile environment.

Aspirator cannulas also are constructed so that the vacuum pump is connected through a hosing to the handle and the vacuum air passageway runs through the handle to the cannula. To connect or disconnect the vacuum with the cannula requires that a technician turn the vacuum pump off by a switch means at the pump or that the physician himself use a footswitch to turn it off. This is inconvenient because the surgeon cannot personally and directly control the application of the amount of vacuum since the pump is not in a sterile environment. Further, because of the distance of the pump and pump hosing to the cannula tip a vacuum rise time of six to eight seconds is typical.

Accordingly, the primary object of the present invention is to provide an improved surgical aspirator cannula designed for surgical aspiration procedures, such as the removal of fatty tissues from the body.

Another object of the present invention is to provide an improved surgical aspirator cannula design and technique which allows for the easy, ready and sterile interchangeability of different cannulas of different styles during the aspirating procedure.

A further object of the present invention is to provide an improved surgical aspirator cannula design which reduces the vacuum rise time after the surgeon has positioned the cannula in the wound and requested that the vacuum be applied to the cannula tip.

A still further object of the present invention is to provide an improved surgical aspirator cannula design which allows the surgeon to personally, directly and conveniently control the application of the vacuum to the cannula tip.

Another object of the present invention is to provide an improved surgical aspirator cannula design which provides a clear viewing area between the surgeon's hand and the cannula and to the interior of the cannula so that the aspiration procedure can be easily and immediately observed.

A further object is to provide an improved surgical aspirator cannula design wherein the cannulas thereof can be easily interchanged in a sterile environment during an aspirating procedure.

A still further object is to provide an improved design o the cannula element of a surgical aspirator wherein the cannula element is disposable and is easily inserted and removed from the aspirator handpiece during a surgical aspirating procedure.

Another object is to provide an improved surgical aspirator construction which automatically vents any residual vacuum in the distal cannula element in the wound when the aspirating suction force thereto is stopped.

A further object is to provide an improved surgical aspirator cannula suitable for liposuction procedures in which fatty tissue and the like can be freely aspirated through the entire length of the aspirator without clogging.

Other objects and advantages of the present invention will become more apparent to those persons having ordinary skill in the art to which the present invention pertains from the following description taken in conjunction with the accompanying drawings.

SUMMARY OF THE INVENTION

Directed to achieving the foregoing objects and overcoming the problems with prior surgical aspirating devices, a preferred surgical aspirator cannula according to this invention comprises an aspirator handpiece having an aspirator conduit longitudinally therethrough, a hollow cannula probe which is removably connectable by a securing assembly at the distal end of the handpiece, and a valve assembly built into the handpiece which controls the application of suction pressure to the cannula probe. The valve assembly is positioned just forward of the handgrip portion of the handpiece. The valve assembly includes a thumb actuated switch pad disposed on top of the valve plunger, and the plunger has a bore laterally therethrough. When the plunger via the switch pad is depressed the bore aligns with the aspiration conduit and suction pressure is applied to the cannula. The depressed switch pad can be slid forward to lock in the valve "open" position. When the switch pad is unlocked and released, a bias spring forces the plunger up to a "closed" position blocking the aspiration conduit. A groove on the forward surface of the plunger vents any residual vacuum, when the valve is closed, in the cannula to atmosphere.

The cannula is formed by an elongated hollow probe with one or more openings at its distal end, and a hollow cannula lock overmolded to the proximal end. The lock comprises a barrel member and a locking pin projecting radially therefrom. A generally tubular hub assembly is press fit into the forward handpiece bore into alignment with the aspiration conduit. A ring lock encircles the forward portion of the hub assembly and is rotatable with respect thereto. Both the ring lock and hub assembly have longitudinal slots engaging their forward surfaces. With the slots aligned the locking pin is inserted therein. The ring lock is rotated drawing the pin back into the rearward angular portion of the ring lock groove thereby securing the cannula to the handpiece.

BRIEF DESCRIPTION OF THE DRAWINGS

FIG. 1A is a side view of a portion of the handle of the surgical aspirator cannula of FIG. 1 illustrating an alternative preferred design.

FIG. 17 is a top plan view of another preferred surgical aspirator cannula of the present invention.

FIG. 18 is a front view of the surgical aspirator cannula of FIG. 17.

FIG. 19 is a cross-sectional view of the surgical aspirator cannula of FIG. 17 wherein the valve assembly is shown in dotted lines in its "up" or "closed" position.

FIG. 20 is a front view of the tip of the surgical aspirator cannula of FIG. 19.

FIG. 43 is a top view of a first cannula design adapted to be removably secured in the surgical aspirator cannula of FIG. 17.

FIG. 44 is an end view of the cannula of FIG. 43.

FIG. 45 is a top view of a second cannula design of the present invention.

FIG. 46 is an end view of the cannula of FIG. 45.

FIG. 47 is a top view of a third cannula design.

FIG. 48 is an end view of the cannula of FIG. 47.

FIG. 49 is a top view a fourth cannula design.

FIG. 50 is an end view of the cannula of FIG. 49.

FIG. 51 is a top view of a fifth cannula design.

FIG. 52 is an end view of the cannula of FIG. 51.

FIG. 53 is a top view of a sixth cannula design.

FIG. 54 is an end view of the cannula of FIG. 53.

FIG. 55 is a top view of a seventh cannula design.

FIG. 56 is an end view of the cannula of FIG. 55.

FIG. 57 is a top view of an eighth cannula design.

FIG. 58 is an end view of the cannula of FIG. 57.

FIG. 59 is a top view of a ninth cannula design.

FIG. 60 is an end view of the cannula of FIG. 59.

FIG. 61 is a top view of a tenth cannula design.

FIG. 62 is an end view of the cannula of FIG. 61.

FIG. 63 is a top view of an eleventh cannula design.

FIG. 64 is an end view of the cannula of FIG. 63.

FIG. 65 is a partial elevational view of the forward portion of the cannula of FIG. 63.

DETAILED DESCRIPTION OF THE PREFERRED EMBODIMENTS

Figure 1:
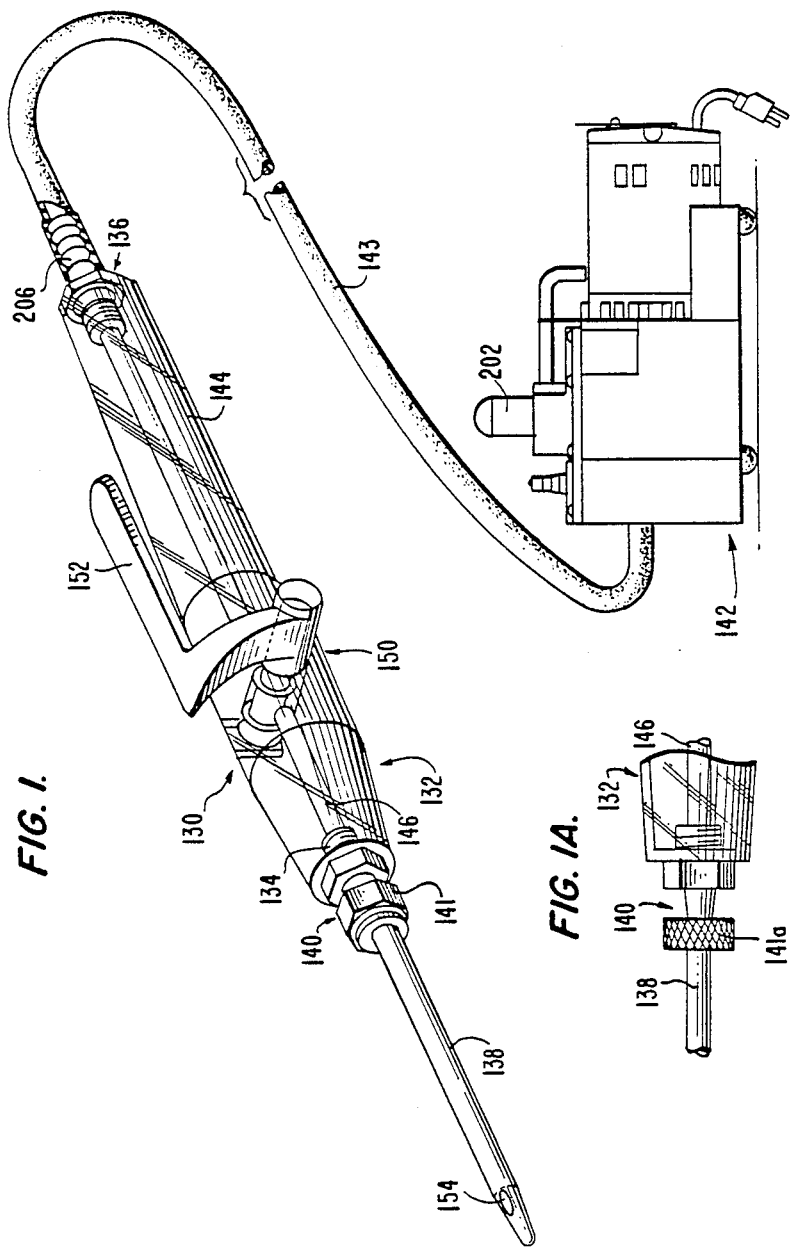
FIG. 1 is a perspective view of a surgical aspirator cannula of the present invention.

A surgical aspirator cannula of the present invention is illustrated generally at 130 in FIG. 1. It is seen to basically comprise a handle shown generally at 132 having a distal port 134 and a proximal port 136, a cannula 138 secured by a cannula connecting assembly shown generally at 140 to the distal end of the handle, and a vacuum pump shown generally at connected via a hosing 143 to the proximal end of the handle. Although the forward nut 141 of the cannula connecting assembly 140 is shown in FIG. 1 as having a hexagonal shape, another preferred design is to provide a round nut with a knurled outer surface as shown in FIGS. 1A at 141a.

Figure 2:
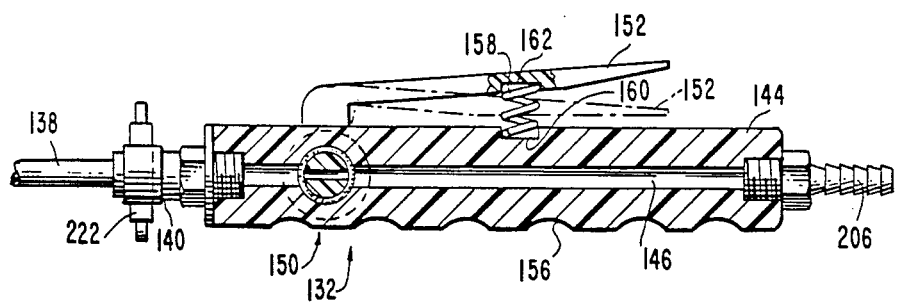
FIG. 2 is a side elevational view of the handle of the surgical aspirator cannula of FIG. 1 illustrating the operation of the hand-operated lever thereof.

Handle 132 is shown to include a body member 144 of a plastic material, such as Delrin, or a clear Lexan, autoclavable at two hundred and seventy degrees Fahrenheit, formed in a slender elongated configuration and being about five to seven or six inches long and about one inch in diameter A preferably straight air passage or conduit 146 is provided extending longitudinally through the body member 144 communicating the distal and proximal ports 134, 136 of the body member. A valve assembly 150 is constructed in the body member 144 to intersect the conduit 146, and is operable, according to one design of this invention, by a hand-operated lever 152 movable between first and second positions. In the first position the conduit 146 is blocked such that the vacuum from the pump 142 does not communicate with the distal port 134 of the body member 144 and thus the cannula 138. In the second position the conduit 146 is opened so that the vacuum can communicate with the distal port 134 and blood, tissue and the like can be aspirated through the tip opening 154 of the cannula when inserted into the body and through the conduit 146 to the pump 142. The lever 152 is configured in an "L" shape so as to be easily grasped by the surgeon's hand. When grasping the handle his fingers rest in finger grips or knurls 156 formed on the bottom surface of the body member 144, as best shown in FIG. 2. The lever 152 is normally biased in its "up" position by a bias spring 158, which is seated in a C-shaped groove 160 on the top surface of the body member 144 and similarly attached at the lower surface 162 of the lever 152. Bias spring 158 biases the lever 152, and thus the valve assembly 150, into the first position closing the conduit 146. Then when the surgeon wants to aspirate after positioning the cannula 138, he simply depresses the lever 152, and the conduit 146 is opened.

Figure 4:
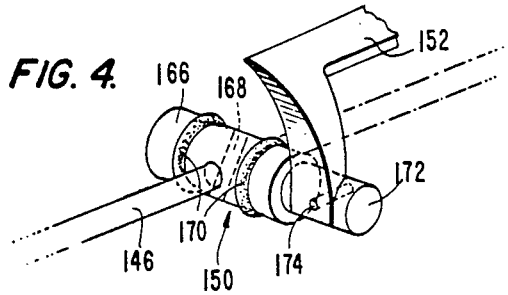
FIG. 4 is a perspective view of the valve assembly and lever of the handle of FIG. 2 shown in isolation for clarity's sake.
Figure 5:
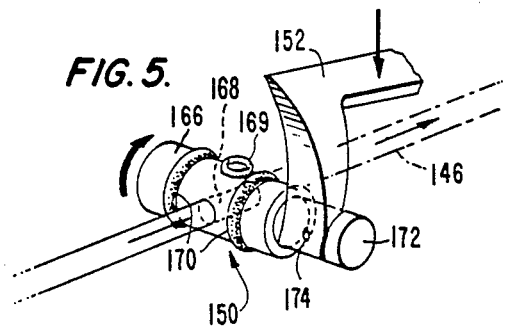
FIG. 5 is a view similar to FIG. 4 illustrating the valve assembly in the "open" position.

The operation of the valve assembly 150 is best illustrated in FIGS. 4 and 5, which show the valve assembly 150 as comprising a ball-type valve wherein a cylinder 166 is provided disposed laterally through the body member 144. The cylinder 166 has a bore or air passageway 168 extending laterally through it through its central portion. When the valve assembly 150 is in the first position, as illustrated in FIG. 4, the air passageway 168 does not communicate with the conduit 146 and thus air does not flow. However, when the valve assembly 150 is moved to the second position as shown in FIG. 5 the air passageway 168 is aligned with the conduit 146 and air flows freely as indicated by the arrow in FIG. 5. An O-ring 169 is secured to the surface of cylinder 166 between the ports of air passageway 168 to provide a seal when the valve assembly 150 is in its "off" or first position. A pair of O-rings 170 encircles the cylinder 166 on opposite sides of the air passageway 168 to maintain an effective air seal. The cylinder 166 also has an extension cylinder arm 172 extending out from the outer surface of the body member and to which the "L" shaped lever 152 is connected via a connector pin 174.

Figure 6:
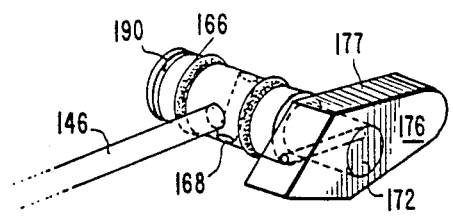
FIG. 6 is a view similar to FIG. 4 illustrating an alternative design for the lever of the valve assembly.
Figure 7:
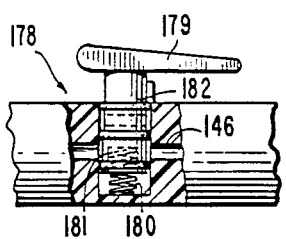
FIG. 7 is a side view of an alternative design of the valve assembly having portions thereof broken away for the sake of clarity.

An alternative design for the lever of the ball valve is illustrated in FIG. 6, which shows a rotating valve knob 176 being provided in lieu of the previously-described lever design. Valve knob 176 is easily rotated between the first and second positions by the surgeon's thumb engaging upper surface 177 as his hand grasps the body member 144.

Figure 8:
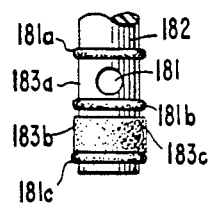
FIG. 8 is an enlarged, fragmentary view of the cylinder of the valve assembly of FIG. 7.
Figure 9:
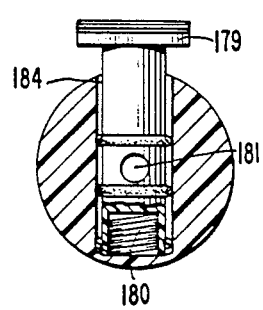
FIG. 9 is a cross-sectional view of the valve assembly of FIG. 7 illustrating the valve in the "open" position.
Figure 10:
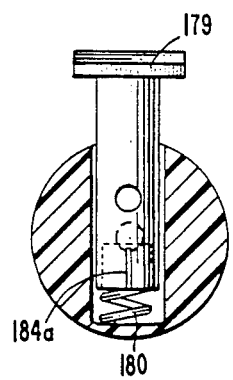
FIG. 10 is a view similar to FIG. 9 illustrating an alternative valve design in the "closed" position.

An alternative design of the valve assembly is illustrated in FIGS. 7–10 generally at 178. Valve assembly 178 is a push button design having a lever or push button 179 which operates against compression return spring 180 to position the passageway 181 so that it communicates with the conduit as in the "open" position of FIG. 9. O-rings 181a, 181b and 181c encircle the one-half inch diameter cylinder 182 and define a "flow" cylinder area 183a over passageway 181 and between O-rings 181a and 181b and a "no flow" are a 183b between O-rings 181b and 181c when in the "closed" position as illustrated in FIG. 10. If carefully constructed though with a close tolerance match an effective seal may thereby be defined and the O-rings would not then be required, as depicted in FIG. 10. An annular rubber seal 183c encircles the cylinder in the "no flow" area 183b and adjacent to O-ring 181a, as shown in FIG. 8. An anti-rotation key 184 prevents cylinder 182 from rotating in its bore. A groove or slot 184a in the lower portion of the cylinder, as illustrated in FIG. 10, allows any residual vacuum in the cannula to be vented or to escape atmosphere.

Figure 3:
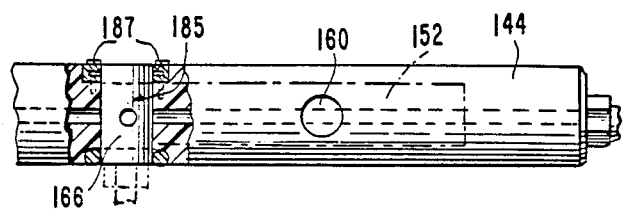
FIG. 3 is a fragmentary top plan view of the handle of FIG. 1 illustrating the ball valve seat assembly.
Figure 11:
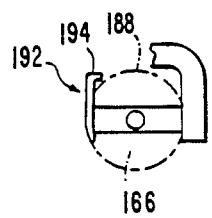
FIG. 11 is a view showing the valve assembly in isolation with an alternative means for locking the valve assembly in place in the body member.
Figure 12:
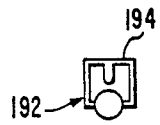
FIG. 12 is a front elevational view of the clip of the locking means of FIG. 11 illustrated in isolation.

The cylinder 166 of the valve assembly is installed and is held in position in the handle by means of a ball valve seat 185 as shown in FIG. 3. Seat 185 extends laterally through the handle and is formed of stainless steel tube 186 secured with three vlier screws 187 positioned at one hundred and twenty degrees and with four set screws. An alternative design for a seating and retaining assembly for the valve assembly is shown in FIG. 11 wherein a channel 188 is formed laterally through the handle and the cylinder 166 is positioned therein. The cylinder 166 is provided at its outer end with a circumferential groove 190 as shown in FIG. 6. A retaining clip 192 is inserted in this groove and when pressed down towards the body member the valve assembly 150 is locked in place, and by simply raising the upper flange 194 of the clip 192 the valve assembly 150 is unlocked. The clip 192 is shown in isolation in its front view of FIG. 12.

Thus, as can be appreciated, the vacuum pump 142 can be turned on and the ball valve assembly 150 will be in its normal first or "closed" position. The vacuum though extends all the way to the valve assembly quite near to the cannula 138. Then when it is desired to aspirate, the lever 152 is moved to its second or depressed position thereby opening the valve assembly 150, and the vacuum very quickly is released to the tip of the cannula 138. Due to the proximity of the valve assembly to the tip of the cannula there is virtually an instantaneous rise time for the vacuum thereby quickening the aspirating procedure. Also, it is less likely that the surgeon will move the cannula 138 out of position relative to the wound during this virtually instantaneous rise time after he has positioned it in the patient's wound. It further does not require the constant presence of a technician to operate the non-sterile pump 142. The handle of lever 152 is formed of autoclavable materials and is always in the sterile environment and thus the switching mechanism for activating the vacuum is also within the sterile environment.

The pump 142 can be of any suitable design. One pump which can be used is the GAST single stage model 5BA-1-GF82X pump. 29.99 inches of mercury. A filter 202, such as the "Coalescent Oil Removing Filter" manufactured by the Master Neumatic Detroit, Inc., can be installed on the exhaust port of the pump 142 to remove the oil mist so that bacteria does not escape into the surgical environment. Further, a filter such as a 0.1 micron in line filter can be added so that the fatty tissues which do not go into the trap of the pump will be contained. Hosing 143 operatively connects the vacuum pump 142 to the handle 132, and a barbed hose fitting 206 at the proximal end of the body member is provided on which the hosing 143 is fitted and secured.

Figure 13:
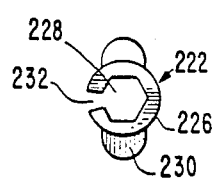
FIG. 13 is a front plan view illustrating in isolation the cannula key of the cannula of FIG. 2.
Figure 14:
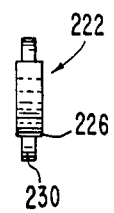
FIG. 14 is a side elevational view of the cannula key of FIG. 13.
Figure 15:
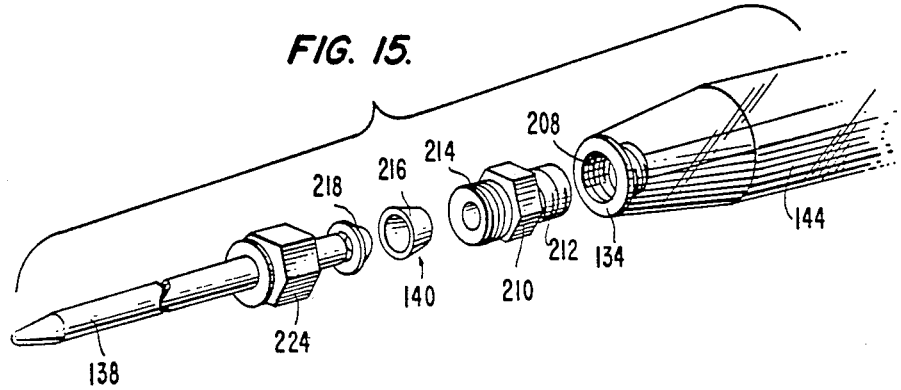
FIG. 15 is a perspective view of the cannula connecting means for the cannula of FIG. 1 wherein the components thereof are illustrated in exploded relation.

The cannula connecting assembly 140 is best illustrated in FIG. 15 wherein it is seen that the distal end of the body member has a threaded port 208. An adaptor 210 is provided having a threaded male member 212 at one end adapted to and threadably engaged in the distal port 208 and a threaded member 214 at its other end. Two interconnecting ferrules 216, 218 are provided, the proximal ferrule 216 fitting into the cone-shaped opening of the adaptor 210 and the distal ferrule 218 fitting into the proximal ferrule 216 and also over the end of the cannula 138. When threaded into position as shown in FIG. 2, for example, the cannula key 222 is fitted over the cannula nut 224 (or 141) and manually threaded to tighten the ferrules 216, 218 onto the smooth end of the cannula 138 and secure it in place. A novel cannula key 222 formed of any suitable autoclavable plastic material is best shown in FIGS. 13 and 14. It comprises a circular body member 226 having a hexagonally-configured opening 228 through it shaped to engage over the hexagonal cannula nut 224. Two ears 230 are secured to the body member 226 at diagonally opposite locations and the ears 230 are adapted to be grasped and rotated to tighten or loosen the nut 224 relative to the ferrules 216, 218. An opening 232 is formed through the body member 226 to the cannula key opening 228 as shown in FIG. 13. The cannulas 138 then can be provided in a variety of configurations adapted to the different uses, and including different lengths, diameters and tip configurations. The port opening configurations also can be varied including the provision for a series of adjacent port openings. These differently configured cannulas are autoclaved and positioned to be easily accessed by the surgeon or nurse who is in the sterile environment during the surgical procedure. Thus, by placing the cannula key 222 of the present invention over the cannula nut 224 and turning it, the cannula 138 is loosened first, then removed from its connection to the body member 226, and then another differently-configured cannula 138 can be inserted through the nut, the nut tightened by turning the cannula key and the new cannula thereby secured in position.

Figure 16:
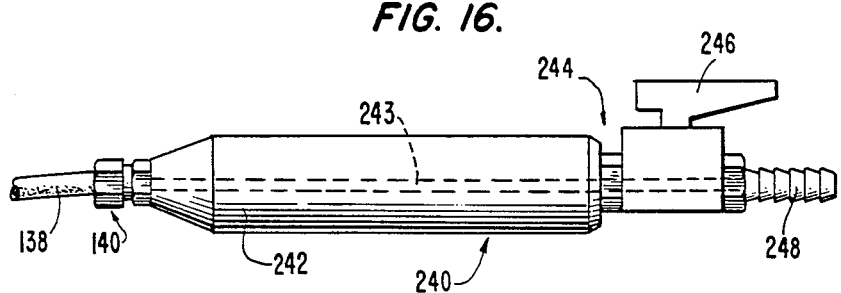
FIG. 16 is a side elevational view of an alternative handle design for the surgical aspirator cannula of the present invention.

An alternative design handle 240 of the present invention is illustrated in FIG. 16. As shown, the cannula connecting assembly 140 can be the same as that shown in FIG. 11, and the body member 242 of the handle will be conventional construction formed of autoclavable plastic and having the conduit 243 extending straight all the way through it. At the proximal end of the handle a select position ball valve 244 is provided which can be easily operated by the surgeon's hand as he holds the body member 242. Similar to the construction of valve assembly 150 of FIGS. 4, 5 and 6, the select-position ball valve 244 will have open and closed positions and a lever 246 or other type of knob which can be physically moved to position the ball valve assembly in the desired position. A tubing barb 248 extends out from the select-position ball valve 244 and the hosing 143 from the vacuum pump 142 connects onto it in a conventional manner.

Another surgical aspirator cannula construction of the present invention is shown generally at 302 at FIGS. 17-20. Surgical aspirator cannula 302 is basically comprised of an elongated body member 304 having a distal end 306, a distal port 308, a proximal end 310 and a port 312 at the proximal end. An aspiration conduit 314 passes longitudinally straight through the body member 304 communicating the distal and proximal ports 308, 312. The conduit 314 has no bends or turns whereat fatty tissue or the like can build up thereby clogging it. A valve assembly shown generally at 316 is supported by the body member 304 and is positioned in the aspiration conduit 314. A cannula securing assembly shown generally at 318 is secured to the distal end 306 of the body member 304. It defines a distal port 320 into which the proximal end of a cannula, such as any of those illustrated in FIGS. 43-65, can be easily inserted, secured and then removed for replacement purposes.

Figure 21:
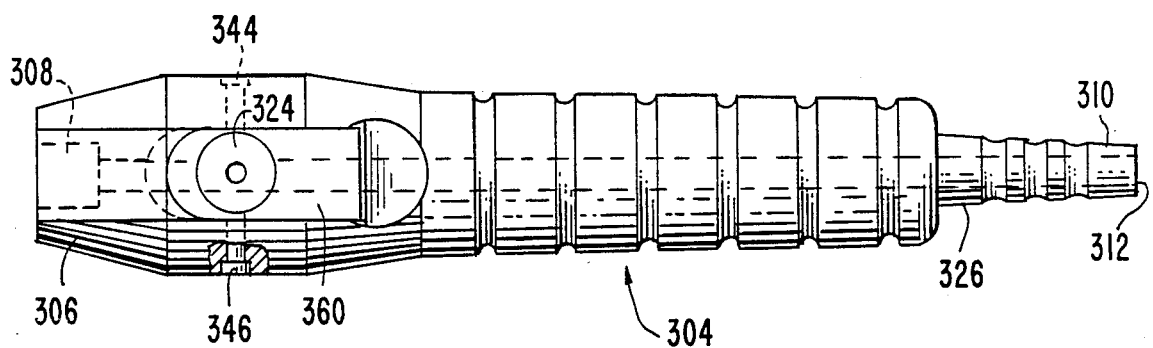
FIG. 21 is a top view of the elongated body member of the surgical aspirator cannula of FIG. 17.
Figure 22:
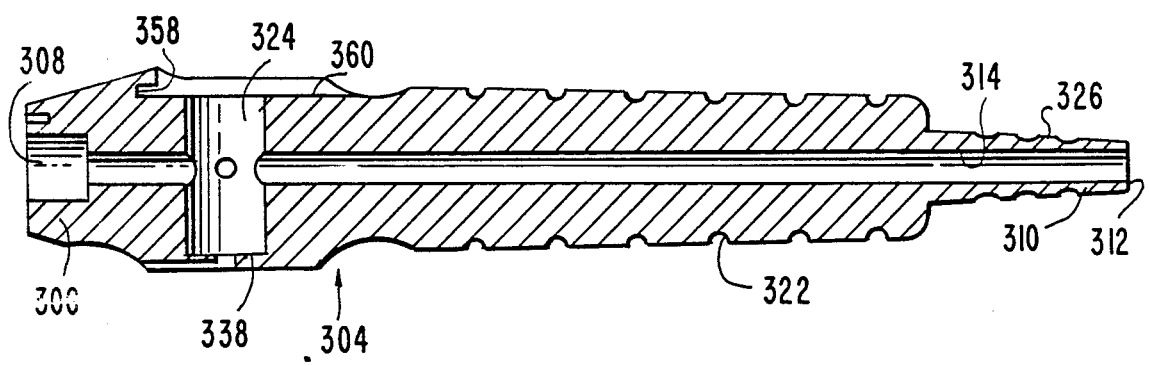
FIG. 22 is a longitudinal cross-sectional view of the body member of FIG. 21.
Figure 23:
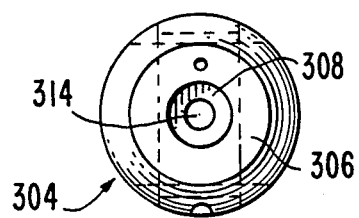
FIG. 23 is a front view of the body member of FIG. 22.

The body member 304 is shown in isolation FIGS. 21-23, and can be formed for example of an aluminum alloy. An operator's knurled hand-grip portion 322 is formed at the proximal end. A vertical bore 324 engages the upper surface at a central or forward location thereof and the valve assembly 316 is built therein. An elongated barbed tube 326 extends rearwardly of the hand-grip portion 322 and a suction hose can be secured thereon for communicating the aspiration conduit with a suction or vacuum pump such as is shown in FIG. 1.

Figure 24:
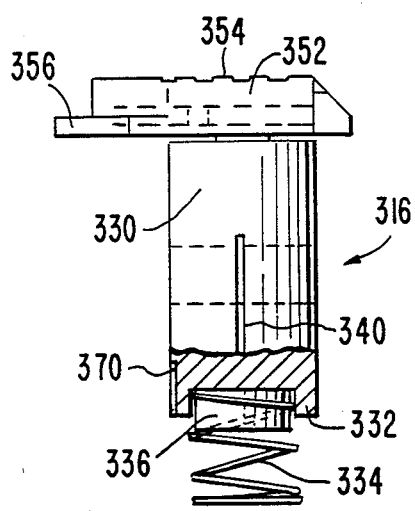
FIG. 24 is a side view of the slide valve assembly of the surgical aspirator cannula of FIG. 17 having portions thereof broken away for the sake of clarity.
Figure 25:
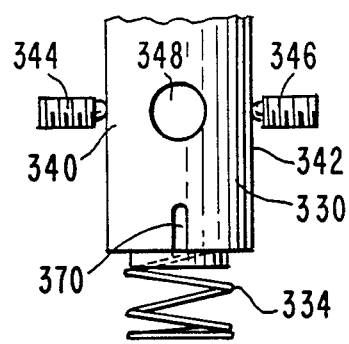
FIG. 25 is an end view of the piston of the slide valve assembly of FIG. 24 illustrating the operation of the guide means.

The valve assembly 316 is shown in isolation in FIG. 24. It is seen to comprise a cylindrical piston or plunger 330 which is fitted with a close tolerance of about one-thousandth of an inch in the vertical bore 324 of the body member 304. An annular ring 332 is formed at its lower end to define a spring seat in which the upper end of a coil spring 334, with a annular spring seal 336 disposed thereabout, is secured. The lower end of the coil spring 334 seats on a bottom surface 338 of the vertical bore 324. A pair of laterally-disposed grooves 340, 342 is formed on the outer surfaces of the plunger 330. Two oppositely positioned vlier ball screws 344, 346 are secured facing each other across the bore 324 in openings in the body member 304 as shown in FIG. 21. The tip ends of these ball screws 344, 346 are precisely positioned to fit into their respective grooves 340, 342, and the plunger 330 will be precisely guided without rotation in its vertical movement in the body member 304 as is depicted in FIG. 25.

The plunger 330, which is shown in isolation in FIGS. 26–29, defines a plunger bore 348 passing laterally therethrough. This bore 348 has the same diameter as the diameter of the aspiration conduit 314. When the valve assembly 316 is in its "open" position, the plunger bore 348 is in perfect alignment with the aspiration conduit 314 and the suction pump produces a suction force through the entire body member 304. The plunger 330 is in its "down" position when the valve assembly 306 is "open". When the plunger 330 is positioned in its "up" position, the plunger bore 348 is disposed above the aspiration conduit 314 and the plunger 330 then blocks or closes the aspiration conduit 314. In fact the suction then in the rearward portion of the aspiration conduit 314 holds the plunger 330, which is closely fitting in the bore 324, tightly against the rear side of the bore thereby providing a complete seal therebetween.

The coil spring 334 at the base of the plunger 330 biases the plunger to its "up" or valve assembly "closed" position. When a downward force is exerted on the top head member 350 of the plunger sufficient to overcome this biasing force the plunger 330 is pushed downward until it is in its "down" or "open" position. This force can be exerted conveniently by the thumb of the operator when he is grasping the hand-grip portion 322 of the body member 304. A trigger or switch pad 352 is disposed on the head member 350 and provides the surface 354 on which the operator's thumb rests and exerts the downward force. When the plunger 330 is in its "down" position the switch pad 352 can be slid forwardly on the head member 350 so that the forward edge 356 of the switch pad 352 slides into a groove 358 of a lock member 360 on the top of the body member 304. This locking groove 358 and lock member 360 are best shown in FIG. 22. The plunger 330 is then locked against the upward bias of the coil spring 334 in its "down" position. The plunger 330 is unlocked by simply sliding the switch pad 352 rearwardly out of the locking groove 358. A shallow track for the sliding switch pad 352 is formed on the upper forward surface of the body member 304.

Figure 34:
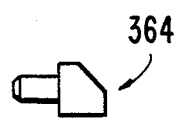
FIG. 34 is a side view of the valve slide stop member of the slide valve assembly of FIG. 24.
Figure 35:
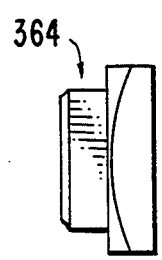
FIG. 35 is a top view of the valve slide stop member of FIG. 34.
Figure 36:
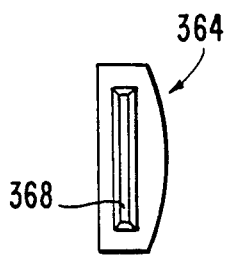
FIG. 36 is an end view of the valve slide stop member of FIG. 35.
Figure 26:
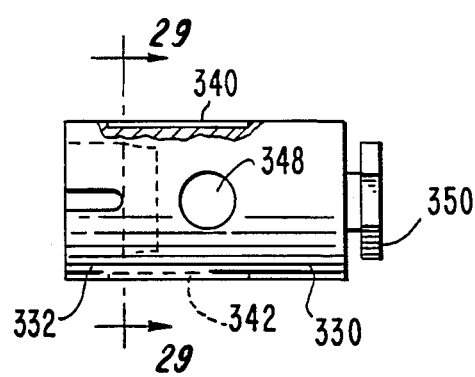
FIG. 26 is a fragmentary end view of the valve plunger of the slide valve assembly of FIG. 24.
Figure 27:
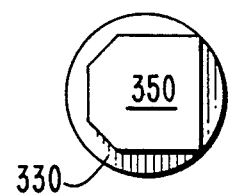
FIG. 27 is a top view of the valve plunger of FIG. 26.
Figure 28:
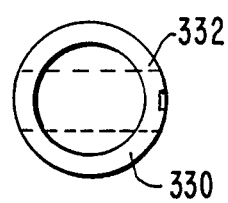
FIG. 28 is a bottom view of the valve plunger of FIG. 26.
Figure 29:
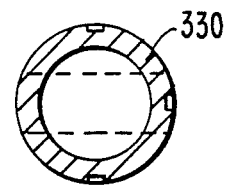
FIG. 29 is a cross-sectional view taken along line 29—29 of FIG. 26.
Figure 30:
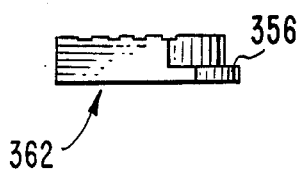
FIG. 30 is a side view of the valve slide member of the slide valve assembly of FIG. 24.
Figure 31:
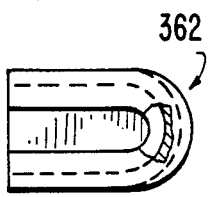
FIG. 31 is a bottom view of the valve slide member of FIG. 30.
Figure 32:
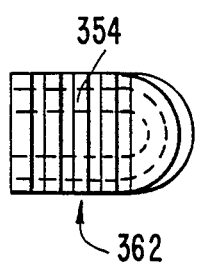
FIG. 32 is a top view of the valve slide member of FIG. 30.
Figure 33:
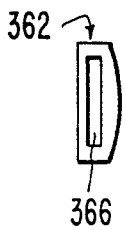
FIG. 33 is an end view of the valve slide member of FIG. 32.

The switch pad 352 is comprised of two portions—the forward portion or valve slide member 362 as illustrated in FIGS. 30–33 and the rear portion or valve slide stop member 364 as shown in FIGS. 34–36. The valve slide member 362 and the stop member 364 can be formed of stainless steel. The slide member 362 has a channel 366 therethrough corresponding to the configuration of the head member 350, so that the valve slide member 362 can be slid into position rearwardly onto the head member 350. The stop member 364 similarly has a corresponding slot 368 which fits onto the rear end of the head member 350. The upper surface 354 of the switch pad 352 defines a plurality of lateral ridges providing a rough engaging surface for the operator's thumb.

Accordingly, the controlled application of a vacuum or suction pressure to the distal end 306 of the body member 304, and thereby to the cannula secured thereto, is quick and easy. With the valve assembly 316 in its normal "up" or "closed" position and the aspirator cannula 302 operatively connected to a vacuum pump, such as through a hosing secured to the barbed tube 326, the vacuum pump is turned on and exerts a force of about twenty-nine inches of vacuum pressure. With the pump turned on the vacuum force is effective all the way to the rear surface of the plunger 330, which is only inches away from the tip of the cannula. When it is desired to apply this suction force to the wound, as with the cannula tip inserted through an incision or wound to the localized fatty tissue deposit, the operator simply rests his thumb on the switch pad 352 and presses the plunger 330 down against the bias of the coil spring 334. When pressed down the plunger bore 348 is in perfect alignment with the aspiration conduit 314 and the vacuum pressure then quickly, in fact nearly instantaneously due to the proximity of the plunger 330 to the tip of the cannula, is applied to the tip of the cannula. By sliding the switch pad 352 forward into the locking groove 358, the valve assembly 316 is locked in its "down" or "open" position and the operator or surgeon can then release his thumb from the switch pad 352. This locking procedure secures the plunger 330 in its "down" position so it is not accidentally released up and also allows the operator's thumb to be removed so it does not tire from exerting continual pressure against the bias of the spring 334. The surgeon can then conduct his aspiration procedure. When he wants to stop the vacuum pressure in the wound he places his thumb on the switch pad 352, moves the switch pad rearwardly and allows the plunger 330 which is biased upward by the coil spring 334 to rise. The plunger 330 then blocks and effectively seals the aspiration conduit 314 and no further suction pressure is then exerted on the cannula.

Any residual vacuum pressure in the forward portion of the aspiration conduit 314 and in the cannula is automatically released according to this invention when the valve assembly 316 is moved to its "closed" position. An elongated vacuum vent groove 370, which is about 3/16 of an inch long, 62/1000 of an inch wide, and 20/1000 of an inch deep, is formed on the forward surface of the plunger 330. An upper portion of this vent groove 370 communicates with the forward portion of the aspiration conduit 314 when the plunger 330 is in its "up" position and the lower end of the groove 370 communicates with the atmosphere, as from the lower end of the groove out through the chamber 371 of the coil spring 334 and out the central lower chamber outlet 371a, as shown in FIG. 19. Thus, any residual vacuum in the forward conduit portion is automatically and quickly release through the vent groove 370 to the atmosphere. It is important to have this venting feature since any residual vacuum can cause body matter such as blood vessels to be sucked to the tip cannula, and then when the cannula is removed from the wound the blood vessels could be pulled out thereby damaging the wound.

Figure 37:
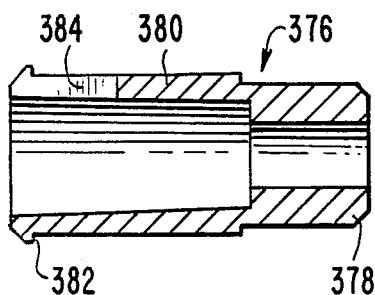
FIG. 37 is a longitudinal cross-sectional view of the cannula hub of the surgical aspirator cannula of FIG. 17.
Figure 38:
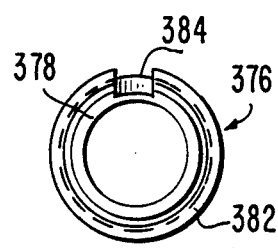
FIG. 38 is a front view of the cannula hub of FIG. 37.

The cannula securing assembly 318 for securing any of the cannulas of the present invention is shown in the forward portions of FIGS. 17 and 19. The securing assembly 318 is formed by a ring lock 374 as illustrated in isolation in FIGS. 40-42, and a cannula hub 376 as shown in isolation in FIGS. 37 and 38. The hub 376 is formed of a proximal sleeve 378 and a distal sleeve 380 connected thereto. It is seen in FIG. 3 that the proximal sleeve 378, although having a greater wall thickness, has a smaller diameter than that of the distal sleeve 380. The proximal sleeve 378 is sized and configured to be press fit into the distal bore 308 at the distal end 306 of the body member 304. At the distal tip of the distal sleeve 380 an abutment barb or ring 382 is formed providing a rear abutment surface. A slot 384 on the upper surface on the distal sleeve 380 passes through the forward tip and the annular ring 382 about half way back in the distal sleeve.

Figure 41:
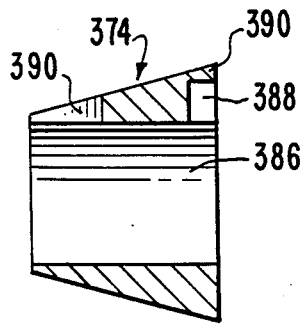
FIG. 41 is a longitudinal cross-sectional view of the ring lock of FIG. 39.
Figure 42:
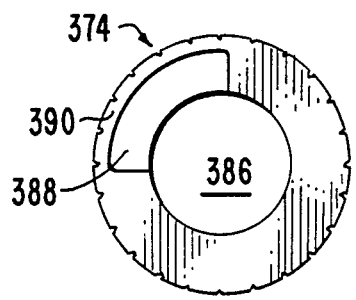
FIG. 42 is an end view of the ring lock of FIG. 41.

The ring lock 374 defines a truncated cone with a cylindrical passageway 386 therethrough, as depicted in FIG. 1 for example. The passageway 386 is sized so that the ring lock 374 can be slid forward on the cannula hub until positioned around the distal sleeve. With the ring lock 344 in place on the cannula hub 376 the proximal sleeve 378 of the cannula hub 376 is then press fit into the distal bore 308 of the body member 304. The ring lock 374 can then be rotated about the longitudinal axis of the hub 376, but cannot move axially forward because of the abutment ring 382 or axially rearward because of the adjacent body member 304. An arcuate groove 388 is formed on the upper rearward surface 390 of the ring lock 374 as shown in FIGS. 41 and 42. A forwardly projecting pin of the body member 304 fits into this arcuate groove 388 and by abutting the ends of the groove prevents a more than generally ninety or one hundred degree rotation of the ring lock 374 about the hub 376, as can be better understood from FIG. 42.

Figure 39:
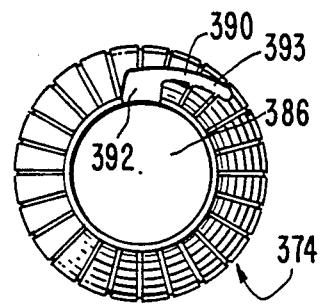
FIG. 39 is a front view of the ring lock of the surgical aspirator cannula of FIG. 17.
Figure 40:
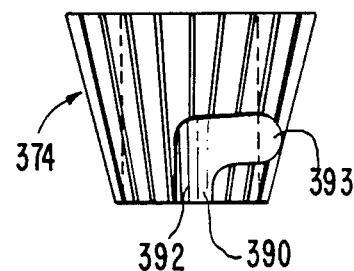
FIG. 40 is a top view of the ring lock of FIG. 39.

The ring lock 374 has a longitudinal slot 392 on its upper surface and engaging its forward end as shown in FIGS. 39, 40 and 41. After extending rearward a distance, the slot then curves at an angle of slightly greater than ninety degrees or preferably ninety-five degrees therefrom. This is seen in its plan view in FIG. 40 and due to the truncated cone shape of the ring lock 374 appears in FIG. 39 as well. This forward portion 392 of the slot (the angled rearward portion thereof is designated by reference number 393) can be aligned with the slot 384 of the cannula hub and then the ring lock 374 rotated with respect to the cannula hub 376. This construction and technique is used to secure and release a disposable cannula from the handpiece or surgical aspirator cannula 302.

Many different sizes and configurations of cannulas for different surgical procedures or portions thereof are possible, such as three and six millimeter diameters, and examples of them are shown in FIGS. 43-65. Each of these cannulas show generally at 393 includes an elongated cannula probe 394 and a plastic cannula lock 396 secured at its proximal end. The cannula lock 396 and the elongated probe 394 are both hollow and the cannula lock 396 is overmolded in alignment with the end of the probe 394 to withstand a minimum fifteen pound pull-out force. At the distal end of the probe 394 one or more smooth-edged holes are formed through which the fatty tissue, fluids and the like can be sucked into the probe 394, through the probe and the surgical aspirator cannula 302 and to the pump. The cannula of FIG. 43 has a single circular hole 400; the cannula of FIG. 45 has a single oval hole 402; the cannula of FIG. 47 has three oval holes 404 spaced one hundred and twenty degrees apart; the cannula of FIG. 49 has two oppositely-disposed holes oval holes 406; and the cannula of FIG. 51 has three longitudinally spaced oval holes 410, 412, 414. These openings are approximately 0.250 inch from the forward tip of the cannulas, and the outer diameters of the probes 394 of the cannulas of FIGS. 43-52 are 0.118 inch.

In contrast, the distance from the probe tip to the forward hole surface of the cannulas of FIGS. 53-60 is 0.38 inches and the outer diameters of the cannulas of FIGS. 53-62 are 0.236 inch. The cannula of FIG. 61 has its opening 416 engaging the tip of the probe 394 to thereby define a longitudinal slot extending rearward about 0.44 inch; each of the other cannulas has a closed distal end. The opening 418 of the cannula of FIG. 53 is a circle; the cannula of FIG. 55 has an opening 420 which is oval; the cannula of FIG. 57 has three openings 422, 424, 426 configured similar to that of FIG. 55 and spaced longitudinally; the three openings 428 of the cannula of FIG. 59 are oval and spaced one hundred and twenty degrees apart; and the opening 430 in the cannula of FIG. 63 is oval. The probe 394 of the cannula of FIG. 63 is in the shape of a spatula with an outer diameter as shown by dimension 432 of 0.236 inches and an outer diameter as shown by dimension 434 of 0.312 inch and in a side view it slopes towards the tip as shown in FIG. 65.

Figure 66:
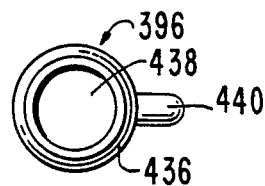
FIG. 66 is an end view of a cannula lock of a cannula of the present invention illustrated in isolation.
Figure 67:
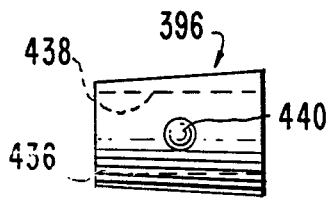
FIG. 67 is an elevational view of the cannula lock of FIG. 66.

The cannula lock 396 for any of these cannula designs is shown in isolation in FIGS. 66 and 67 and comprises a barrel or slightly truncated cone 436 having a cylindrical hole 438 therethrough and a pin 440 attached to the top and extending out therefrom a distance of 0.340 inch to the center of the hole 438. The pin 440 has a width of 0.093 inch. As previously mentioned, this cannula lock 396 is overmolded securely to the probe 394 at the proximal end thereof. The pin 440 then will project radially out therefrom, and the cannula lock 396 is positioned relative to the probe 394 so that the pin 440 is oriented to be one hundred and eighty degrees from the end hole or line of holes of the probe 394.

Then with the forward slot portion 392 of the ring lock 374 aligned with the slot 384 of the cannula hub 376, the cannula lock 396 is inserted into the passageway defined by the cannula hub 376 with the pin 440 fitting into the aligned slots 384, 392. After the pin 440 has been pushed as far back as it will go, the ring lock 374 is rotated so that the pin 440 is drawn into the rearward portion 393 of the ring lock slot and the pin 440 and thereby the cannula 393 are drawn rearwards securing the cannula 393 to the body member 304.

In a single liposuction procedure the surgeon will usually use three or so cannulas 393 of different styles as shown herein for different aspects of the surgical procedure, such as feathering, long stroking, and short stroking. It is of course necessary that the cannulas always remain in the sterile environment. It is expected that each of these cannula which are disposable will be provided in sterile packages. These packages will then be removed by the nurse or other technician, who is in the sterile environment and who is assisting in the aspiration surgery. The technician then will insert the cannula lock 396 and the pin 440 into the aligned slots 384, 392 and when the cannula is pushed back, the operator or surgeon who is grasping the body member 304 with one hand (for a right handed person this would typically be his right hand) and will turn with the fingertips of his other (left) hand the outer ribbed surface of the ring lock 374 thereby securing the cannula 393 to the body member 304. His hands which are not in the sterile environment will thereby never touch the sterile cannula, and it is not necessary that he change handpieces during an aspiration procedure on a patient.

From the foregoing detailed description, it will be evident that there are a number of changes, adaptations, and modifications of the present invention which come within the province of those skilled in the art. However, it is intended that all such variations not departing from the spirit of the invention be considered as within the scope thereof as limited solely by the claims appended hereto.

What is claimed is:

1. A surgical aspirator cannula comprising:
   an elongated body member having a distal end and a proximal end,
   said body member defining a longitudinal aspiration conduit passing therethrough between said distal end and said proximal end,
   a securing means for securing a proximal end of an elongated cannula to said distal end to communicate the cannula proximal end with said aspiration conduit,
   said proximal end being connectable to a source of vacuum,
   a valve assembly positioned at least partially in said body member and in said aspiration conduit,
   said valve assembly being positionable in a first valve position closing said conduit so that the source of vacuum is blocked relative to said distal end port, and in a second valve position opening said conduit so that the source of vacuum communicates with said distal end port,
   a hand-operated switch means supported by said body member and operatively connected to said valve assembly for moving said valve assembly between said first and second valve positions,
   said switch means being positionable in a first switch position wherein said valve assembly is in said first valve position and in a second switch position wherein said valve assembly is in said second valve position,
   a biasing means for biasing said valve assembly into one of said first and second valve positions,
   said switch means including a manually-movable switch pad,
   said valve assembly including a piston disposed transversely to said aspiration conduit and having a bore extending transversely therethrough,
   said piston closing said conduit when said valve assembly is in said first valve position,
   said piston opening said conduit by having said bore aligned with said conduit when said valve assembly is in said second valve position, and
   said biasing means biasing said piston relative to said conduit.

2. The aspirator cannula of claim 1 wherein said switch pad is positioned radially closer to the center line of said body member when in said second switch position than in said first switch position.

3. The aspirator cannula of claim 1 wherein said body member defines on its upper surface a longitudinal track in which said switch pad can slide.

4. The aspirator cannula of claim 1 further comprising a locking means supported by said body member for locking said switch means in said first switch position.

5. The aspirator cannula of claim 4 wherein said switch pad is movable longitudinally relative to said body member.

6. The aspirator cannula of claim 4 wherein said biasing means biases said switch pad radially out from said body member when in said first switch position.

7. The aspirator cannula of claim 4 wherein said locking means includes a grooved structure supported by said body member and into which said switch pad slides.

8. The aspirator cannula of claim 1 wherein said piston defines a groove extending generally longitudinally therealong and communicating the forward conduit portion of said conduit forward of said piston, when said valve assembly is in said first valve position, with the atmosphere, to vent any residual vacuum valve in said forward conduit portion and in a cannula secured to said body member by said securing means, after said valve assembly has been positioned in said first valve position.

9. The aspirator cannula of claim 8 wherein said groove is vertically disposed and is positioned on a forward surface of said piston.

10. The aspirator cannula of claim 1 wherein said elongated body member defines thereon a user hand grip portion, and said switch pad is positioned forward of said user hand grip portion and so as to be movable between said first and second switch positions by the thumb of a user's hand that is grasping said user hand grip portion.

11. The aspirator cannula of claim 1 wherein said valve assembly includes a generally flat head member secured at the top of said piston, and along which said switch pad can slide.

12. The aspirator cannula of claim 1 wherein said body member defines a bore therein, said piston is disposed in said bore, and said bore is configured to provide a close tolerance fit with said piston and to thereby provide an effective seal therebetween.

13. The aspirator cannula of claim 1 wherein said biasing means comprises a coil spring positioned within said body member and having an upper end engaging a lower surface of said piston and a lower end biasing against said body member, and said coil spring biases said valve assembly to said first valve position.

14. The aspirator cannula of claim 13 wherein said piston defines at its lower end a spring seat, and further comprising a sealing member in said spring seat and surrounding said upper end of said coil spring.

15. The aspirator cannula of claim 1 wherein said piston includes a longitudinal groove on its outer surface and said body member includes a guide member projecting towards said piston and riding in said longitudinal groove as said valve assembly moves between said first and second valve positions.

16. The aspirator cannula of claim 15 wherein said guide member comprises at least one vlier ball screw.

17. The aspirator cannula of claim 1 further comprising a venting means connected to said valve assembly for automatically venting any residual vacuum in the forward portion of said conduit forward of said valve assembly when said valve assembly is positioned to said first valve position.

18. The aspirator cannula of claim 1 wherein said body member defines a forward bore at said distal end, and said securing means comprises a cannula hub member having a proximal hub end positioned in said forward bore, a distal hub portion, a hub bore passing therethrough and communicating with said conduit, a hub slot engaging a forward surface of said distal hub portion and extending rearwardly therefrom, and said securing means further comprises a ring lock member disposed about said distal hub portion, at least partially rotatable about said distal hub portion and including a ring lock slot engaging a forward surface thereof and extending generally rearwardly therefrom, and said ring lock slot, by twisting said ring lock member about said distal hub portion, being alignable with said hub slot to receive a locking pin of a cannula therein.

19. A surgical aspirator cannula comprising:
an elongated body member having a distal end and a proximal end,
said body member defining a forward bore at said distal end,
said body member defining an aspiration conduit passing generally longitudinally straight therethrough between said distal end and said proximal end,
said proximal end being connectable to a source of vacuum,
a valve assembly connected to said body member,
a securing means for securing a proximal end of a cannula to said distal end to communicate the cannula proximal end with said aspiration conduit,
said securing means including a cannula hub member having a proximal hub end positioned in said forward bore, a distal hub portion, a hub bore passing therethrough and communicating with said conduit, and a hub slot engaging a forward surface of said distal hub portion and extending rearwardly therefrom,
said securing means further including a ring lock member disposed about said distal hub portion, at least partially rotatable about said distal hub portion, and including a ring lock slot engaging a forward surface thereof and extending generally rearwardly therefrom, and
said ring lock slot, by twisting said ring lock member about said distal hub portion, being alignable with said hub slot to receive a locking pin of an elongated cannula therein.

20. The aspirator cannula of claim 19 wherein said ring lock slot is configured to draw the locking pin positioned therein rearwardly relative to said body member and to thereby secure the cannula to said body member as said ring lock member is rotated relative to said hub slot.

21. The aspirator cannula of claim 20 wherein said ring lock slot includes a longitudinal slot portion engaging said forward surface, and a lateral slot portion extending generally laterally relative to said longitudinal slot portion and from a rearward end thereof.

22. The aspirator cannula of claim 21 wherein said lateral slot portion defines an angle greater than ninety degrees with said longitudinal slot portion.

23. The aspirator cannula of claim 22 wherein said angle is ninety-five degrees.

24. The aspirator cannula of claim 19 wherein said ring lock member defines by its outer surface a truncated cone.

25. The aspirator cannula of claim 19 wherein said ring lock member has an outer lock surface defining a friction increasing means disposed to be accessible by a user's fingers, and said friction increasing means comprises a plurality of longitudinal ribs.

26. The aspirator cannula of claim 25 wherein said ring lock member includes a rear surface and a full rotation blocking slot on said rear surface.

27. The aspirator cannula of claim 19 wherein said proximal hub end is press-fitted into said hub bore.

28. The aspirator cannula of claim 19 wherein said ring lock member is rotatable more than an insubstantial amount and substantially less than three hundred and sixty degrees relative to said cannula hub member.

29. The aspirator cannula of claim 19 wherein said cannula hub member includes a preventing means for preventing said ring lock member from being slid forwardly thereof.

30. The aspirator cannula of claim 29 wherein said preventing means comprises an abutment structure at a forward end of said cannula hub member and projecting radially out therefrom.

31. The aspirator cannula of claim 30 wherein said abutment structure comprises an annular structure.

32. The aspirator cannula of claim 19 wherein said ring lock member is slid forwardly onto said cannula hub member before said proximal hub member is fitted into said hub bore.

33. The aspirator cannula of claim 19 wherein said valve assembly is positionable in a first valve position closing said conduit so that the source of vacuum is blocked relative to said distal end port and in a second valve position opening said conduit so that the source of vacuum communicates with said distal end port.

34. The aspirator cannula of claim 33 further comprising a hand-operated means supported by said body member and operatively connected to said valve assembly for moving said valve assembly between said first and second valve positions.

35. The aspirator cannula of claim 34 further comprising a venting means connected to said valve assembly for automatically venting any residual vacuum in the forward portion of said conduit forward of said valve assembly when said valve assembly is moved from said second to said first valve position.

36. A surgical aspirator cannula comprising
an elongated body member having a distal end and a proximal end,
said body member defining a longitudinal aspiration conduit passing therethrough between said distal and proximal ends,
said proximal end being operatively connectable to a source of vacuum,
said body member defining at said distal end a distal end port having a threaded opening,
a removable securing means for removably securing a proximal end of an elongated cannula to said distal end port so that a longitudinal passageway of the cannula communicates with said aspiration conduit,
said securing means comprising an adaptor having distal and proximal threaded male connectors and a nut secured between them, and an adaptor passageway extending therethrough, said proximal threaded male connector threadably engaging in said threaded opening by rotating said adaptor nut relative to said body member, a ferrule means fitting in said distal threaded male connector, and a cannula nut positionable around the cannula and when tightened causing said ferrule means to grip the cannula end and thereby secure the cannula to said distal end, and said ferrule means comprising a cone-shaped first ferrule fitting into said distal threaded male connector and a second ferrule fitting into said first ferrule and have a distal rim which said cannula nut engages.

37. The aspirator cannula of claim 36 wherein said cannula nut has a multi-sided circumferential surface, and said securing means comprises a cannula key having a body portion with a multisided opening therethrough and a pair of ears projecting from said body portion, said body portion fitting around said cannula nut such that when rotated by grasping and turning said ears the surface of said opening engages and turns said multi-sided circumferential surface.

38. The aspirator cannula of claim 36 wherein the proximal portion of the cannula end has a generally smooth circumferential surface and fits into said ferrule means.

39. The aspirator cannula of claim 36 wherein said cannula nut threads onto said distal male connector.

40. The aspirator cannula of claim 36 wherein said body member is formed at least in part of a clear material providing a window through which said conduit therein can be seen.

41. The aspirator cannula of claim 40 wherein said window is at the hand-grip area of said body member.

42. The aspirator cannula of claim 36 wherein said cannula nut is round and has a knurled outer circumferential surface.

43. A cannula member for a surgical aspirator cannula device, said cannula member comprising:
an elongated hollow cannula having a cannula distal portion and a cannula proximal end,
said cannula defining at said cannula distal portion at least one cannula opening in through which fatty tissue and the like can be aspirated,
a cannula lock, and
said cannula lock including a locking sleeve encircling said cannula proximal end and overmolded thereto, and a locking pin secured to said locking sleeve and projecting radially out therefrom.

44. The cannula member of claim 43 wherein said cannula opening is disposed on one side of said cannula.

45. The cannula member of claim 43 wherein said locking pin is disposed one hundred and eighty degrees relative to said cannula opening.

46. The cannula member of claim 43 wherein said cannula has a distal cannula tip and said cannula opening engages said distal cannula tip.

47. The cannula member of claim 43 wherein said at least one cannula opening comprises at least two longitudinally-spaced openings.

48. The cannula member of claim 43 wherein said opening defines a circle, an oval or a slot.

49. A surgical aspiration method comprising the steps of:
providing a surgical aspirator cannula having an elongated body member with a body member distal end, a cannula hub member at said body member distal end and having a hub slot, and a lock ring member at least partially rotatable about said cannula hub member and having a ring lock slot,
providing a cannula member including an elongated cannula having an aspiration opening at the distal portion thereof and a cannula lock at the proximal end thereof, said cannula lock including a radial cannula pin,
grasping said body member in one hand of a surgeon,
with said hub groove and ring lock slot aligned, inserting with one hand, which is in the sterile environment, of a medical personnel other than the surgeon, said radial cannula pin into said aligned slots, and
thereafter, twisting with the other hand of the surgeon said lock ring member relative to said body member to thereby secure said cannula to said body member.

50. The method of claim 49 wherein said twisting causes said cannula to be drawn further towards said body member.

51. A surgical aspirator cannula comprising:
an elongated body member having a distal end and a proximal end,
said body member defining a longitudinal aspiration conduit passing therethrough between said distal end and said proximal end,
a securing means for securing a proximal end of a cannula to said distal end to communicate the cannula proximal end with said aspiration conduit,
said proximal end being connectable to a source of vacuum,
a valve assembly positioned in said body member and in said aspiration conduit,
said valve assembly including an elongated member positioned at least partially in said body member and movable relative thereto,
said valve assembly being positionable by moving said elongated member to a first valve position closing said conduit so that the source of vacuum is blocked relative to said distal end port and to a second valve position opening said conduit so that the source of vacuum communicates with said distal end,
a hand-operated means supported by said body member and operatively connected to said valve assembly for moving said elongated member between said first and second valve positions, and
said valve assembly including a venting means for automatically venting any residual vacuum in the forward portion of said conduit forward of said valve assembly when said elongated member is moved from said second to said first valve position.

52. The aspirator cannula of claim 51 wherein said venting means comprises a groove on said elongated member and communicating said conduit forward portion with the atmosphere when said elongated member is in said first but not in said second valve position.

53. The aspirator cannula of claim 52 wherein said elongated member comprises a cylinder.

54. The aspirator cannula of claim 53 wherein said cylinder is rotatable relative to said body member.

55. The aspirator cannula of claim 53 wherein said cylinder is axially displaceable relative to said body member.

56. The aspirator cannula of claim 52 wherein said hand-operated means comprises a lever means squeezable towards said body member and operatively connected to said elongated member.

57. The aspirator cannula of claim 52 wherein said hand-operated means comprises a push button operatively connected to said elongated member.

58. The aspirator cannula of claim 52 wherein said hand-operated means comprises a rotatable knob.

59. The aspirator cannula of claim 52 wherein said hand-operated means comprises a switch pad movable longitudinally and laterally relative to said body member.

60. The aspirator cannula of claim 52 wherein said body member defines a chamber, said valve assembly includes a biasing means positioned in said chamber for biasing said elongated member, and said venting means vents through said chamber.

* * * * *